United States Patent [19]

Bosone et al.

[11] Patent Number: 4,599,358

[45] Date of Patent: Jul. 8, 1986

[54] PYRETHROIDS

[75] Inventors: Enrico Bosone; Giuseppe Caprara; Francesco Corda, all of Milan; Franco Gozzo, San Donato Milanese; Augusto Menconi; Paolo Piccardi, both of Milan; Vincenzo Caprioli, San Martino, all of Italy

[73] Assignee: Montedison, S.p.A., Italy

[21] Appl. No.: 209,589

[22] Filed: Nov. 24, 1980

[30] Foreign Application Priority Data

Nov. 26, 1979 [IT] Italy ............................... 27542 A/79

[51] Int. Cl.$^4$ ................. A61K 31/275; A61K 31/215; C07C 121/50; C07C 69/74
[52] U.S. Cl. ................................... 514/521; 514/531; 560/124; 558/407
[58] Field of Search ................. 260/465 D, 112.5 R; 560/124; 424/282

[56] References Cited

U.S. PATENT DOCUMENTS

| | | | |
|---|---|---|---|
| 3,998,868 | 12/1976 | Mizutani et al. | 560/124 |
| 4,291,176 | 9/1981 | Heine et al. | 260/465 D X |
| 4,401,673 | 8/1983 | Martel et al. | 424/282 |
| 4,432,972 | 2/1984 | Karanewsky | 260/112.5 R |

*Primary Examiner*—Delbert R. Phillips
*Attorney, Agent, or Firm*—Morgan, Finnegan, Pine, Foley & Lee

[57] ABSTRACT

There are described 3-phenoxy-benzyl or α-cyano-3-phenoxy-benzyl esters of 2,2-dimethyl-cyclopropanecarboxylic acids substituted in position 3 by a dienic polyhalogenated chain, as well as their use as insecticides and acaricides. Moreover, there are also described the intermediates for their preparation and processes for their preparation.

22 Claims, No Drawings

PYRETHROIDS

The present invention concerns new insecticides and acaricides belonging to the class of pyrethroids, and more particularly, to new cyclopropanecarboxylic esters substituted in position 3 by a dienic chain having from 4 to 8 carbon atoms and halosubstituted, the use of these compounds as insecticides and acaricides, as well as the intermediates and processes for their preparation.

BACKGROUND OF THE INVENTION

There are already known numerous pyrethroid insecticides, some of which combine a good insecticide activity with a sufficient persistence in the field, for instance, "Synthetic Pyrethroids" by M. Elliot—Editors ACS Symposium, Series No. 42, Washington, 1977.

Likewise, there are known pyrethroids substituted in position 3 of the cyclopropylic ring by a dienic chain.

M. Elliot and collaborators have described 5-benzyl-3-furyl-methyl-esters of 2,2-dimethyl-3-butadienyl-cyclopropanecarboxylic acid. See NATURE, No. 244, p. 456 (1973).

These compounds, which are endowed with a high degree of insecticidal activity, rapidly undergo degradation in the presence of air and light (photooxidation), however, and because of this they are not suited for the use in agriculture.

In Japanese Patent Application No. 7411854 by Sumitomo, reported in Chemical Abstracts No. 81, 34599 (1974), there are described esters with lower alcohols of 2,2-dimethyl-3-cyclopropanecarboxylic acids substituted in position 3 by a branched dienic chain having from 4 to 8 carbon atoms and not substituted by halogen.

In Belgian Pat. No. 858,137 (Bayer), there is described a method for the synthesis of intermediates for pyrethroids, among which are esters of 2-($\beta,\delta$, $\delta$-trichloro-1,3-dienyl)-2,2-dimethyl-cyclopropanecarboxylic acid.

However, examples of the preparation of this acid nor of its derivatives have not been given, nor has there been indicated the insecticidal properties or its characteristics.

From the process described in the aforementioned patent, there can be deduced that the above-mentioned carboxylic acid should be prepared starting from 1,1,3-trichloro-6-methylheptatriene. No indications are given regarding the preparation of this compound or of other trienes, nor is there said anything about their use in the synthesis of pyrethroids.

DESCRIPTION OF THE INVENTION

We have now found, and this forms an object of this invention, compounds having the general formula:

$$\begin{array}{c} H_3C \quad CH_3 \\ \diagdown \diagup \\ R^1 \quad R^4 \quad C \\ \diagdown \quad | \quad \diagup \diagdown \\ C=C-C=CH=CH\text{———}CH-C-R \\ \diagup \quad | \qquad\qquad\qquad \| \\ R^2 \quad R^3 \qquad\qquad\qquad O \end{array}$$ (I)

wherein:
R=OH, O-alkyl $C_1$-$C_4$, halogen, $$-O-\underset{R^5}{\underset{|}{CH}}-\bigcirc\!\!\!\!\!\!\!\!\!\!-O-\bigcirc$$

wherein
$R^5$=H, CN, —C≡CH,
$R^1$=F, Cl, Br, $CH_3$, $CF_3$,
$R^2$=F, Cl, Br, —$CF_3$,
$R^3$=H, F, Cl, Br, $CF_3$,
$R^4$=H, F, Cl, Br, $CF_3$;
or $R^2$ and $R^3$ together may form a third bond between the two carbon atoms to which they are bonded.

The compounds of general Formula (I), in which:

$$R = -O-\underset{R^5}{\underset{|}{CH}}-\bigcirc\!\!\!\!\!\!\!\!\!\!-O-\bigcirc$$

are insecticides and acaricides endowed with a high activity and which possess a high persistence of these activities.

The compounds of General Formula (I), wherein R=OH, O-alkyl, halogen, are intermediates for the synthesis of the insecticide compounds.

The synthesis of the compounds which are endowed with an insecticide and acaricide activity is achieved, for instance, by converting a cyclopropanecarboxylic ester or acid of Formula (I), in which R is O-alkyl $C_1$-$C_4$ or OH, to the correspondent acylic halide (I, R=halogen), and by reacting this latter compound with an alcohol having the formula:

$$HO-\underset{R^5}{\underset{|}{CH}}-\bigcirc\!\!\!\!\!\!\!\!\!\!-O-\bigcirc$$ (II)

where $R^5$ has the meanings reported in Formula (I).

As far as the preparation of the new intermediate of Formula (I) is concerned, different procedures are possible, the choice of which depends mainly on the nature of the substituents present in the dienic chain ($R^1$, $R^2$, $R^3$ and $R^4$).

There follows a description of: a process for the synthesis of the compounds of Formula (I), wherein $R^4$ is different from H (method A); a process for the synthesis of the compounds of Formula (I) wherein $R^3$=H (method B); and a process for the synthesis of the compounds of Formula (I) wherein $R^4=H$ (method C).

The compounds of Formula (I) in which $R^3=H$ can be prepared also by a procedure different from Method B described in the present application. The alternative procedure, described in copending Italian Patent Application No. 22566 A/80, comprises reacting a 2-alkenphosphonate with esters of caronic aldehyde. The results are more convenient than Method B.

METHOD A

A lower alkyl ester of 2,2-dimethyl-3-formylcyclopropanecarboxylic acid (1) (caronic aldehyde), as a mixture of geometric isomers or as a single isomer, is made to react according to the Witting reaction with the ilide (2) of a haloalkenyl of formula (3):

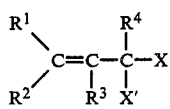  (3)

wherein:
$R^1$, $R^2$ and $R^3$ have the previously specified meanings;
$R^4=F$, Cl, Br, $CF_3$;
X and X' (equal to or different from each other)=Cl, Br.

Scheme 1

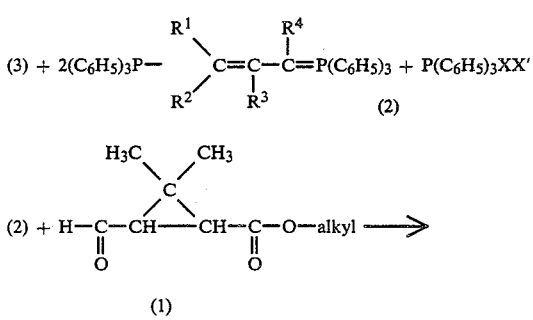

As examples of such compounds of Formula (3), there may be cited:

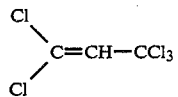

$Cl_2C=CH-CCl_3$

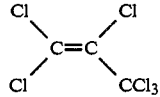

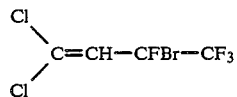

-continued

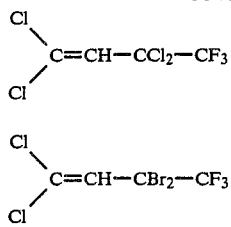

Some of the compounds of Formula (3), and more particularly those of the general formula:

  (III)

wherein: X and X' (equal to or different from each other)=halogen, are new compounds and form another object of this invention.

Their preparation is achieved by dehydrohalogenation of 1,1,1-trifluoro-2,2,4,4,4-pentahalobutanes described below.

Alternatively to the process indicated in Scheme 1 the compounds of Formula (1), wherein $R^4$ is a halogen atom, may be prepared by carrying out a Wittig reaction between a lower alkyl ester of 2,2-dimethyl-3-formyl-cyclopropanecarboxylic acid (λ) and a polyhaloalkane of Formula (4):

  (4)

and by subjecting the resulting product of this reaction to a dehydrohalogenation with bases, according to Scheme 1b.

Scheme 1b

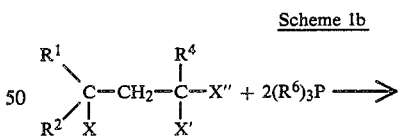

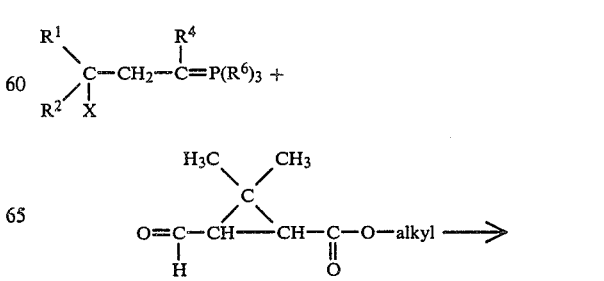

-continued
Scheme 1b

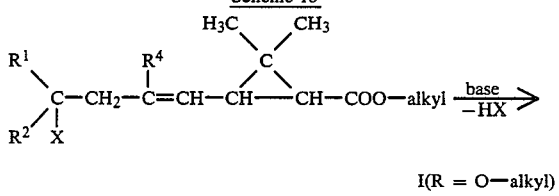

where $R^6$=alkyl, phenyl.

As a further alternative to the process indicated in Scheme 1, the compounds of Formula (I), wherein $R^4$ is either a chlorine or bromine atom, may be prepared by a Wittig reaction between allyl chloride or allyl bromide of the type:

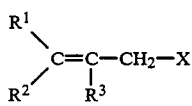

and a lower alkyl ester of 2,2-dimethyl-3-formyl-cyclopropanecarboxylic acid (1), and then by subjecting the resulting dienic product to a halogenation reaction with $Cl_2$ or $Br_2$, followed by dehydrohalogenation.

Scheme 1c

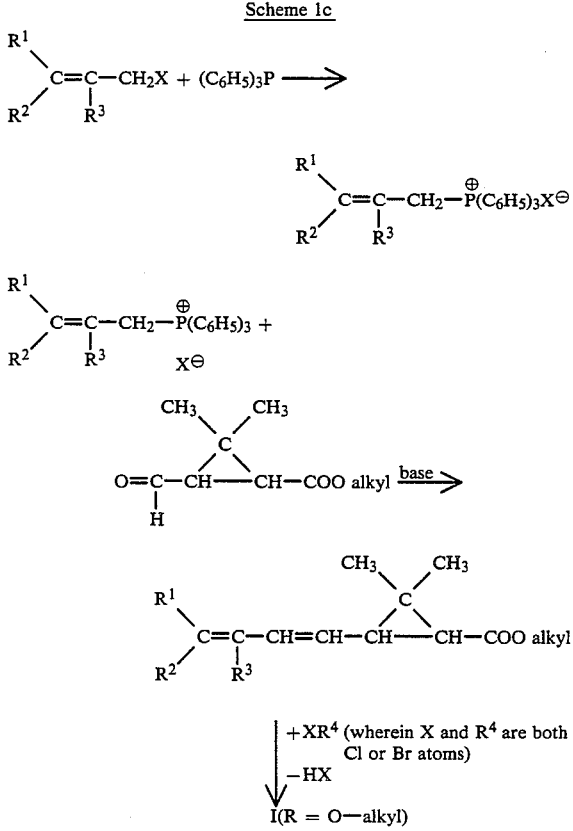

METHOD B

A polyalkane (propane or butane) (4) is additioned with an ester of 3,3-dimethyl-4-pentenoic acid (5, n=1) or 2-etoxycarbonyl-3,3-dimethyl-4-pentenoic acid (5, n=2):

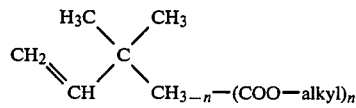

(n=1 or 2), thereby obtaining adduct (6) which, when treated with a base, undergoes in one or more stages, successive dehydrohalogenation with the elimination of three mols of halogenhydric acids optionally followed (in the case n=2) by a decarboxylation.

In the case where the dehydrohalogenation is carried on and $R^2$ is a halogen atom, there are obtained the compounds of Formula (I) in which $R^2$ and $R^3$ together constitute a third bond.

Scheme 2

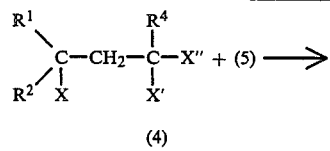

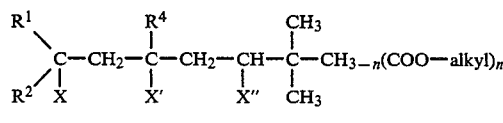

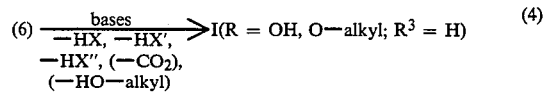

(X, X' and X" (equal to or different from each other)=Cl, Br; n=1 or 2, $R^1$, $R^2$ and $R^4$ have the same meanings as those reported for general Formula (I).)

The polyhaloalkanes of Formula (4), suited for reacting according to reaction (3), are, for instance:
1,1,1,3,3,3-hexahalopropanes,
1,1,1,3,3,3-pentahalobutanes,
1,1,1,2,2,4,4,4-octahalobutanes.

Among these compounds there may be mentioned the following few as examples:
$CCl_3$—$CH_2$—$CCl_3$
$CH_3$—$CCl_2$—$CH_2$—$CCl_3$
$CF_3$—$CCl_2$—$CH_2$—$CCl_3$
$CF_3$—$CBr_2$—$CH_2$—$CCl_2Br$
$CF_3$—$CFBr$—$CH_2$—$CCl_2Br$.

Some of these compounds, namely the 1,1,1-trifluoro-2,2,4,4,4-pentahalobutanes, are new compounds and constitute a further object of the present invention.

Their preparation, which likewise constitutes an object of this invention, is achieved by reacting a polyhaloethane of Formula (7):

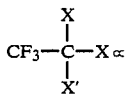

with vinylidene chloride, according to the following:

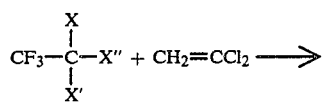  (5)

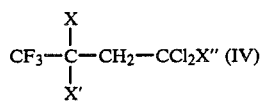 (IV)

wherein X=F, Cl, Br; X' and X" (either equal to or different from each other)=Cl, Br.

Both reactions 3 and 5, in general, are achieved by reacting the haloalkane (4 or 7) with the unsaturated ester (5) or with the vinylidene chloride, in a molar ratio from 1 to 4.

The above indicated reactions are conducted in inert solvents at a temperature between 50° and 200° C. and in the presence of catalytic amounts of radical reaction promoters, such as organic peroxides (tert-butyl-peroxide, benzoyl-peroxide, diacetyl-peroxide), azo-derivatives (azo-bis-isobutyronitrile), U.V. radiation, or in the presence of redox-transfer systems or of metal-carbonyls, etc.

Reaction (4) is conducted according to known techniques, either in a single stage or in a plurality of successive stages, using organic bases (amines), alkaline alcoholates or inorganic bases (NaOH, KOH).

METHOD C

A mixture of cis and trans isomers of esters with lower alcohols of 2,2-dimethyl-3-acetoxymethyl-cyclopropanecarboxylic acid (8) is hydrolyzed with catalytic amounts of sodium ethylate in ethanol, thereby obtaining a mixture of ethyl ester of trans, 2,2-dimethyl-3-hydroxymethyl-cyclopropanecarboxylic acid (9) and of the lactone of the same acid in the cis form (10).

Compounds (9) and (10) may be separated by distillation, and each one may be independently converted into the corresponding 3-bromomethyl derivative, i.e., compound (9), by treatment with triphenylphosphine bromide $(C_6H_5)_3 PBr_2$ and compound (10) by treatment with HBr, thereby obtaining the 3-bromomethyl-derivative of trans, ethyl ester (11-trans) and the 3-bromomethyl-derivative of the cis acid (12) which will then be converted to the corresponding alkyl ester (11-cis).

Intermediates 11-cis and -trans, either separately or in admixture with each other, are converted to the corresponding phosphonium salts (13) by treatment with triphenylphosphine $(C_6H_5)_3P$.

Finally, the phosphonium salts (13) are made to react with an aldehyde of the formula:

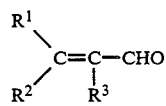 (14)

where $R^1$, $R^2$ and $R^3$ have the same meanings indicated for the general Formula (1).

Thereby are obtained the compounds of Formula (1) wherein R=O-alkyl and $R^4$=H.

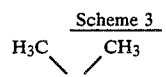

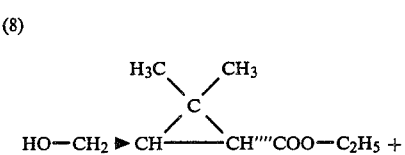

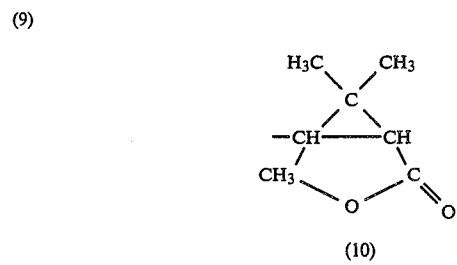

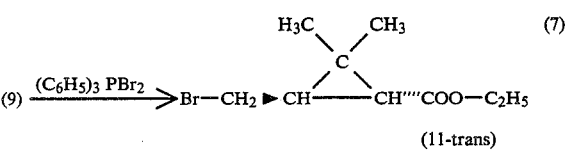

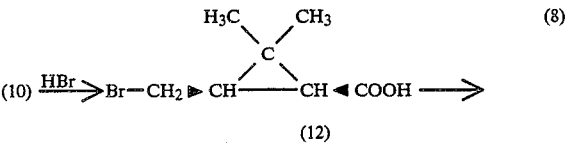

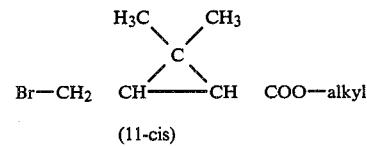

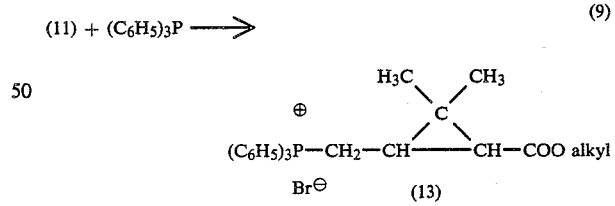

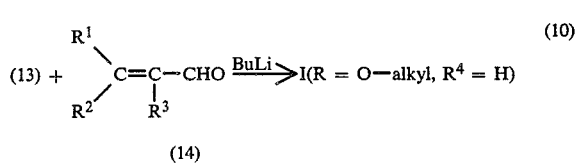

The reactions from (6) to (9) are carried out by applying well known techniques in the art in the transformations of hydroxy acid esters by hydrolysis and lactonization, in the substitution of an OH group by a bromine atom and in the formation of phosphonium salts from bromoalkyl derivatives. The Examples herein give an adequate documentation of the sequence of these reactions.

Wittig reaction (10), although known by itself, has never been applied to halogenated derivatives of acrolein. This reaction is conducted by suspending the phosphonium salt (13) in an anhydrous inert solvent (e.g., tetrahydrofurane), in an anhydrous and deoxygenated nitrogen atmosphere according to that described by L. F. Fieser in "Reagents for Organic Synthesis", J. Wiley & Sons Ed., 1967, page 149. To this suspension is then admixed a stoichiometric quantity of butyllithium dissolved in the same solvent, at a temperature between $-70°$ and $-20°$ C. As soon as the butyllithium has disappeared (as can be checked by carrying out the Gilman test described in "Organic Reactions", 6, 1951, page 352), to the ylide thus prepared is added the aldehyde (14) in slight excess and is then allowed to react at a temperature of between $-20°$ and $0°$ C. Once the reaction has ended, the betainic complex that has formed is preferably decomposed by treatment with a stoichiometric quantity of phosphoric hexamethyltriamide and then with water, in order to obtain the dienic ester I ($R=$O-alkyl, $R^4=$H).

The esters with lower alcohols of 2,2-dimethyl-3-acetoximethyl-cyclopropanecarboxylic acid (compound (8)) have been described in Italian Patent Application No. 24,255 A/79.

As examples of aldehydes of Formula (14) which are suited for the reaction with phosphonic salts (13) according to the Wittig, reaction (10), mention is made of the following:

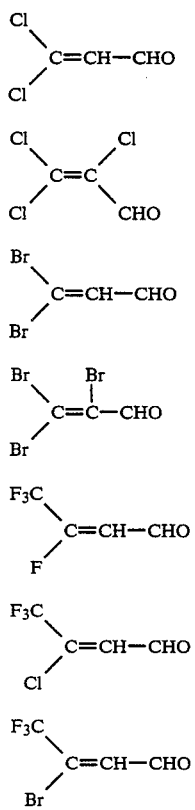

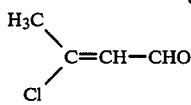

Some of the aldehydes of Formula (14), and more particularly, those having in the β position a $CF_3$ group and one halogen, of formula

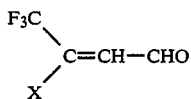  (V)

($X=$F, Cl, Br) are new compounds and form another object of this invention.

Their preparation is achieved by reacting 1,1,1-trifluoro-2,2,2-trihaloethane with a vinyl ether followed by dehydrohalogenation and hydrolysis.

The addition reaction of 1,1,1-trifluoro-2,2,2-trihaloethane to a vinylalkyl ether (or to another vinyloxiderivative, such as for instance vinyl acetate) is conducted in the presence of radical reaction promoters, at temperatures between 0° and 200° C., by operating with an excess of polyhaloethane, with or without solvents. As a radical reaction promoter there may be used one of the following agents: U.V. light, peroxides, transition metal salts such as, for instance, iron or copper salts, in the presence of either primary or secondary amines, or azo-derivatives such as, for instance, azo-bis-isobutyronitrile.

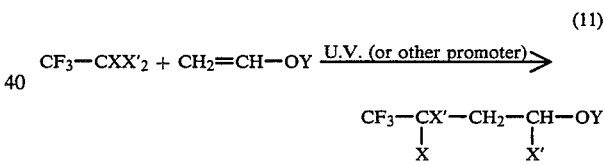  (11)

wherein:
$X=$F, Cl, Br; $X'=$Cl, Br;
$Y=$an alkyl group with from 1 to 5 carbon atoms, or

($R'=$lower alkyl).

Some further examples of the addition of other fluoro alkanes to vinyl ethers have been reported by P. Tarrant, E. C. Stump in the Journal of Organic Chemistry, 29, p. 1198 (1964).

After the adduct is obtained, it is subjected to dehydrohalogenation and hydrolysis of the α-haloether group by treatment with boiling water or with bases or salts developing an alkaline action (e.g., $Na_2CO_3$, $NaHCO_3$) in an aqueous medium (equation 12).

Alternatively, the dehydrohalogenation reaction may be carried out in a stage preceding the hydrolysis, for instance by heating up the adduct to a temperature at which there is a thermal elimination of the halogenhydric acid HX (equation 14).

In turn, the conversion of the α-haloetheric group (when R=alkyl) to an aldehydic group may be achieved by pyrolysis (equation 15) instead of by hydrolysis (equation 13).

A further alternative comprises conducting the hydrolysis reaction in the presence of water, at the boiling temperature, (equation 16), followed by a dehydrohalogenation in the presence of an aqueous base (equation 17).

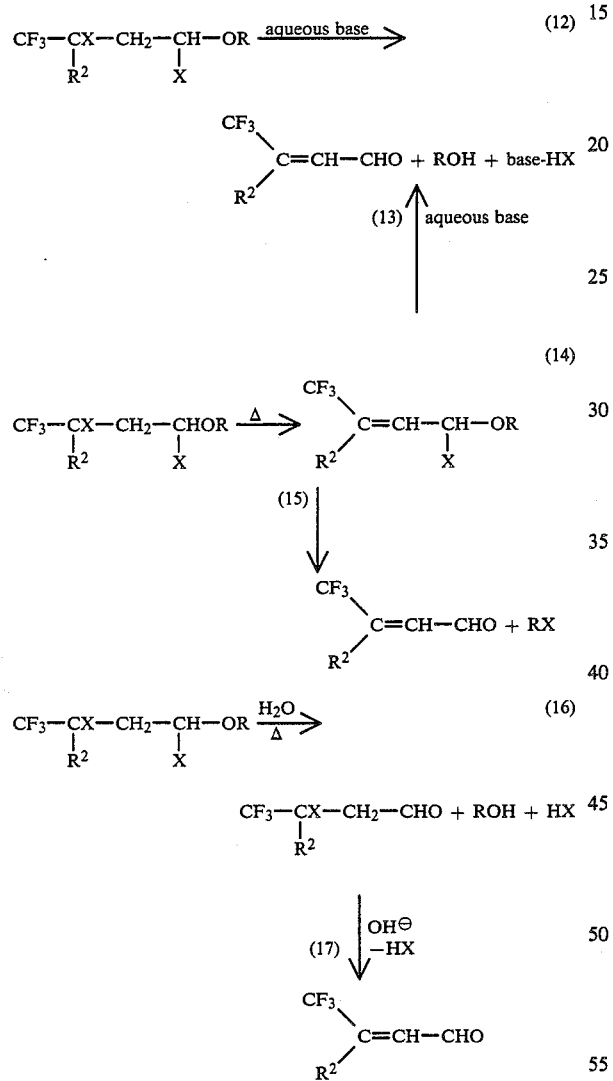

The thermal decomposition reactions (in the absence of water) are conducted at temperatures between 70° C. and 250° C.

With the above indicated methods are thus prepared the compounds of Formula (1) in which R=OH or O-alkyl.

From these compounds, with methods known in the common practice of organic chemistry, it is possible to prepare the acylic halides (I, R=halogen), for instance, by the reaction of acids with thionyl chloride.

From the acylic halides, by reaction with the alcohols of Formula (II), according to known techniques, there are obtained the compounds of Formula (I), wherein:

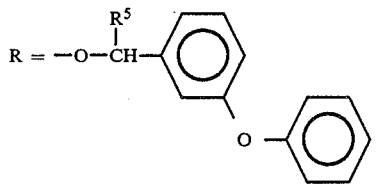

The compounds of Formula (I), in general, are obtained as mixtures of geometrical and configurational isomers due to the particular structure of the molecule which contains asymmetric carbon atoms and double bonds.

The separation of the various mixtures in the various diastereoisomers may be achieved following the techniques usually applied in the normal practice of organic chemistry, such as for instance, chromatographic methods.

Under the spirit of this invention falls the separation and the use of the single isomers or their mixtures or of the mixtures obtained by partial separation of the isomers of the compounds of Formula (I).

The compounds of Formula (I), wherein R is an alcoholic residue of the 3-phenoxy-benzyl alcohol, optionally α-substituted, possess high insecticidal activity against insects belonging to the most important species, from the point of view of their noxiousness in the agricultural and civil fields, such as *hemiptera, lepidoptera, coleoptera* and *blattoidea,* and possess, moreover, a high acaricidal activity, particularly as ovicides. In this latter action they prove by far more active than the best pyrethroids known.

Moreover, they are endowed with a high stability to photo-oxidation, a property that ensures a sufficient persistence of their action, thus allowing also their use in agriculture.

The insecticide compounds of Formula (I) may be applied to a zone where insect control is desired both as technical materials or as suitable compositions or formulations.

Suitable compositions comprise an insecticide compound of Formula (I) as an active ingredient in combination with one or more suitable inert carriers and/or surface active agents, and optionally other active compounds such as other insecticides, acaricides, nematocides, etc.

Suitable formulations include granules, dusts, wettable powders, emulsifiable concentrates, solutions, dispersions and the like.

The active ingredient may be present in a suitable composition at a concentration of from 0.1% to 99% by weight.

While the application rate of the formulations varies widely depending on the type of formulation, the active compound, the mode of application and the environment, an effective insecticidal amount of the active principle must be applied and the practical rate may vary in the range of 0.01 to 3 Kg/hectare.

In order to even further illustrate this invention, there follows a number of Examples.

DESCRIPTION OF THE SPECIFIC EMBODIMENTS

EXAMPLE 1

Preparation of $CF_3$—$CCl_2$—$CH_2$—$CCl_3$

Into a Pyrex glass vial were introduced the following:
- 10 g of 1,1,1-trichlorotrifluoroethane (0.05 mols),
- 5 g of 1,1-dichloroethylene (0.05 mols),
- 0.2 g of diethylamine-chlorohydrate,
- 0.2 g of $CuCl_2.2H_2O$, and
- 8 ml of acetonitrile.

After sealing on a flame, the vial was heated for 24 hours at 120° C. Thereupon, it was cooled down and opened and the content was diluted with 50 ml of methylene chloride and then washed with water (3×100 ml), after which it was anhydrified on sodium sulphate and subjected to distillation in order to remove the solvent and the more volatile fractions consisting mainly of unreacted trichlorotrifluoroethane.

As a residue there were gathered 5 g of a fluid yellowish liquid, mainly consisting of 1,1,1,3,3-pentachloro-4,4-trifluorobutane.

NMR (nuclear magnetic resonance) $\delta = 3.8$ ppm ($CH_2$) in $CDCl_3$.

Mass spectrometry: ($C_4H_2Cl_5F_3$), 247 ($M^+$—Cl), 211 (247—HCl), 151 ($CF_3$—$CCl_2^+$), 117 ($CCl_3^+$), 69 ($CF_3^+$).

EXAMPLE 2

Preparation of: $CF_3$—$CBr_2$—$CH_2$—$CCl_2$ Br

Into a glass flask of 500 cc holding capacity, fitted with a reflux condenser, there were introduced under a nitrogen atmosphere the following reactants:
- 339 g of 1,1,1-trifluoro-2,2,2-tribromoethane (1.056 mols);
- 51 g of 1,1-dichloroethylene (0.526 mols);
- 0.5 g of CuCl; and
- 10 ml of ethanolamine.

This reaction mixture was then heated up at the reflux temperature for 4 hours. After cooling down, the reaction mixture was washed with water until attaining a neutral pH, whereupon it was subjected to distillation. After removal of the excess trifluorotribromoethane overhead, there were gathered 30 g of a fraction with a boiling point between 43° and 45° C. at 0.15 mm Hg, 90% of which was 1,1,1-trifluoro-2,2,4-tribromo-4,4-dichlorobutane as evidenced by mass spectrometry combined with gas-chromatographic separation.

Mass spectrum: peak of molecular ion $C_4H_2F_3Br_3Cl_2$, main fragments: $CF_3$—$CBr_2^+$, $CCl_2Br^+$.

and 10% of which was the dehydrohalogenation product:

Mass spectrography: peak of molecular ion: $C_4HF_3Br_2Cl_2$.

EXAMPLE 3

Preparation of ethyl 3,3-dimethyl-4,8,8-tribromo-6,6-dichloro-9,9,9-trifluorononanoate

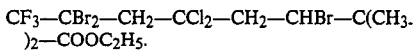

Into a quartz vial were introduced under an atmosphere of nitrogen the following:
- 41.8 g of $CF_3$—$CBr_2$—$CH_2$—$CCl_2Br$ (prepared as described in Example 2); and
- 15.6 g of ethyl 3,3-dimethyl-pent-4-enoate.

The vial was then sealed and irradiated with a high pressure Hanau lamp for 15 hours at 65° C. The content of the vial was then distilled in order to remove the unconverted reactants. The residue (12 g) proved to consist essentially of the desired product (gas-chromatographic analysis).

| Mass fragmentations: $C_{13}H_{18}F_3Cl_2Br_3O_2$ | $M^+/e$ = 269, 189, 161, 155 (main peak) 135, 129, 109, 88, 87 |
|---|---|

EXAMPLE 4

This illustrates the preparation of ethyl 3-(2'-chloro-4'-bromo-4'-trifluoromethyl-butadienyl)-2,2-dimethyl-cyclopropanecarboxylate.

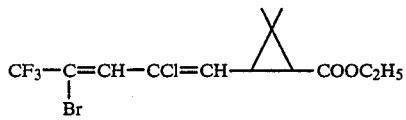

The adduct prepared as described in Example 3 (0.02 mols), was treated with 0.06 equivalents of sodium ethylate in 40 ml of absolute ethyl alcohol at a temperature of 60° C., for 2 hours.

After removal of the solvent, the residue was diluted with methylene chloride, then washed with water, acidified with acetic acid until obtaining a neutral pH, then anhydrified on $CaCl_2$ and then, after removal of the solvent, subjected to fractioned distillation, gathering the fraction that boils at 62°–63° C. at 0.2 mm Hg. This fraction proved to consist of about 65% of the desired product.

EXAMPLE 5 (Method B)

This illustrates the preparation of ethyl 3,3-dimethyl-4,6,6,8,8-hexachloro-octanoate:

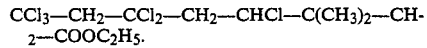

Into a 50 cc flask, fitted with a stirrer and a reflux condenser, connected at the upper end to a calcium chloride valve, there were introduced the following:
- 12.5 g of 1,1,1-3,3,3-hexachloropropane (0.05 mols);
- 8 g of ethyl 3,3-dimethyl-pent-4-enoate (0.05 mols); and
- 1 g of diterbutylperoxide.

The reaction mixture was then heated up to 150° C. for 24 hours. After cooling down, from the mixture was drawn a sample of the product which, by gas-chromatographic analysis, proved to consist of about 50% of the addition product and of minor quantities of hexachloropropane and of ethyl 3,3-dimethylpent-4-enoate that had not reacted. The latter were removed from the reaction mixture by distillation under vacuum, thereby gathering the fractions that boil until a temperature of the vapors of 110° C. at 0.5 mm Hg.

The residue (11 g) was extracted with n-hexane, then purified with active charcoal and subjected to the removal of the solvent in order to give 7 grams of ethyl 3,3-dimethyl-4,6,6,8,8,8-hexachlorooctanoate.

Mass spectrometry: ($C_{12}H_{18}Cl_6O_2$), 404 ($M^+$), 359 ($M^+$—$OC_2H_5$), 333 ($M^+$—$OC_2H_5$—Cl—HCl), 287 ($M^+$—$CCl_3$), 129 ($C(CH_3)_2$—$CH_2$—$COOC_2H_5^+$), 117 ($CCl_3^+$), 87 ($CH_2$—$COOC_2H_5^+$).

EXAMPLE 6 (Method B)

This illustrates the preparation of ethyl 3,3-dimethyl-4,6,6,8,8-pentachloro-9,9,9-trifluoro-nonanoate.

$$CF_3—CCl_2—CH_2—CCl_2—CH_2—CHCl—C(CH_3)_2—CH_2—COOC_2H_5.$$

Into a 50 cc flask fitted with a stirrer and a reflux condenser, connected by its upper end to a $CaCl_2$ valve, there were introduced:

5.7 g of $CF_3$—$CCl_2$—$CH_2$—$CCl_3$ (0.02 mols);
3.1 g of ethyl 3,3-dimethylpent-4-enoate (0.02 mols); and
about half of a solution obtained by dissolving 0.5 ml of $Fe(CO)_5$ in 5 ml of isopropyl alcohol.

This reaction mixture was thereupon heated up under a slight refluxing at about 100° C., and additioned, in 3 hours, with the remaining iron pentacarbonyl ($Fe(CO)_5$) solution. After cooling down the content was then diluted with 50 ml of methylene chloride, then washed with water, anhydrified and finally concentrated under vacuum in order to give 8.5 g of a raw product which was then distilled under vacuum, gathering thereby the fraction boiling at 115°–118° C. (0.15 mm Hg) and which consisted of the desired product.

EXAMPLE 7

This illustrates the dehydrohalogenation of ethyl 3,3-dimethyl-4,6,6,8,8,8-hexachlorooctanoate (1).

To a solution of 2.1 g of (1), prepared as described in Example 5, in anhydrous n hexane (25 ml) there was added a solution of 2 grams of tetramethyl-guanidine in 25 ml of anhydrous n hexane. The reaction mixture was then maintained under stirring for 24 hours at room temperature, after which it was poured into cold water. The hexanic phase was thereupon separated and the aqueous phase was extracted with diethyl ether (50 ml). The heteric phase was recombined with the hexanic phase. The resulting solution was washed with a diluted solution of HCl until attaining a neutral pH. It was then anhydrified with $CaCl_2$ and then concentrated until reaching a constant weight, thus obtaining a raw product (7 g) consisting of compound A (95%) and of compound B (5%).

Compound A: ethyl 3,3-dimethyl-4,6,8,8-tetrachloroocta-5,7-dienoate.

$$Cl_2C=CH—CCl=CH—CHCl—C(CH_3)—CH_2—COOC_2H_5$$

(mixture of cis and trans isomers).

The IR analysis is consistent with the assigned structure.

| $^1$H NMR ($\delta$, ppm): | 1,2 | (9H, methyl groups) |
|---|---|---|
| | 2,15–2,7 | (m, 2H) |
| | 4,15 | (q, 2H,O—$\underline{CH_2}$—$CH_3$) |
| | 4,6–5,2 | (m, 1H) |
| | 5,9–6,5 | (m, 2H) |
| Mass fragmentation: | | ($M^+$/e) |
| $C_{12}H_{16}O_2Cl_4$ | 332 | ($M^+$) |
| | 296 | ($M^+$—HCl) |
| | 260 | ($M^+$—2HCl) |
| | 173 | ($M^+$—3HCl, —$C_2H_5$) |
| | 96 | |

Compound B: ethyl 2,2-dimethyl-3-(2',4',4'-trichlorobuta-1',3'-dienyl)-cyclopropanecarboxylate.

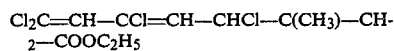

| Mass fragmentation: | |
|---|---|
| $C_{12}H_{15}O_2Cl_3$ | 296($M^+$), 260($M^+$—HCl), |
| | 213($M^+$—$CHCl_2$) |
| | 177($M^+$—HCl—$COOC_2H_5$) |

EXAMPLE 8

Hydrolysis of 2-acetoxymethyl-3,3-dimethyl-carbethoxycyclopropane for obtaining 2-hydroxymethyl-3,3-dimethyl-carbethoxy-cyclopropane trans and 6,6-dimethyl-3-oxa-bicyclo(3,1,0)-hexan(2)one.

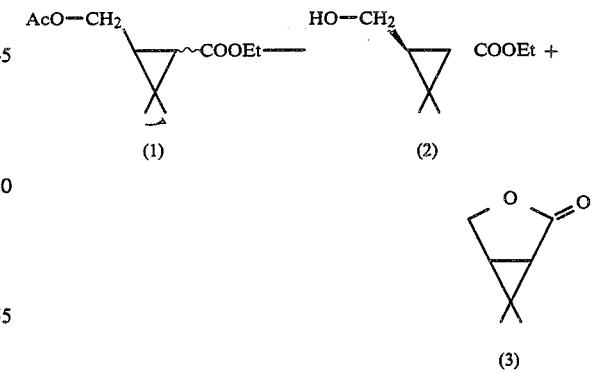

1 mol of (1) was dripped, at a temperature of between 0° and 10° C., into a beaker containing 500 cc of 99% ethyl alcohol and 0.25 mols of metal sodium. This mixture was then kept under stirring at room temperature overnight. Thereafter the solvent was evaporated at 15 mm Hg until obtaining about 250 cc of solution. This was poured into 750 cc of water and ice and was then extracted with methylene chloride (4 times, each time with 150 cc of solvent).

The reunited organic phases were then washed with water until reaching a neutral pH, whereupon they were anhydrified and evaporated, thereby obtaining 140 g of an oil which by gas liquid chromatographic analysis (GLC) appeared to consist for 35% of (3) and for 50% of (2) (yield about 80%).

The raw product was distilled and rectified at 15 mm Hg. There were obtained 0.37 mols of (3) (b.p. at 15 mm Hg=112°–114° C.) and 0.33 mols of (2) (b.p. at 15 mm Hg=132°–134° C.)

IR analysis of (3): 1780 cm$^{-1}$

IR analysis of (2): 3200–3600 cm$^{-1}$, 1715 cm$^{-1}$, 1380–1370 cm$^{-1}$, 1170 cm$^{-1}$, 1020 cm$^{-1}$.

EXAMPLE 9 (Method C)

Preparation of 2-bromomethyl-3,3-dimethyl-carbethoxycyclopropane trans.

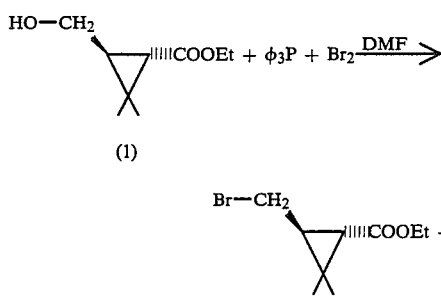

About 0.3 mols of bromine are dripped into a solution of 0.27 mols of 2-hydroxymethyl-3,3-dimethyl-carboethoxycyclopropane (1), 0.28 mols of triphenylphosphine and 300 cc of dimethylformamide, maintaining the temperature at between 50° and 55° C. (dripping time about 30 minutes).

Once the dripping has been completed, the mixture was maintained under stirring at 50° C. for 5 minutes. Thereafter, it was cooled down and then poured into 1.2 liters of water and ice, after which it was extracted with benzene (5 times, each time with 150 cc of solvent).

The reunited organic extracts were then washed with an aqueous sodium bicarbonate solution at 5% concentration, then with a 5% sodium sulphite solution and finally with water until attaining a neutral pH. The mixture was thereupon anhydrified on sodium sulphate and then evaporated, obtaining a raw product of a rubbery appearance. It was then diluted with petroleum ether, and the white solid that precipitated (70 g of triphenylphosphoxide equal to 0.25 mols) was filtered. After evaporation of the solvent there were obtained about 0.25 mols of (2) (yield=90–95%). b.p. (at 0.05 mm Hg)=65°–66° C.

NMR (δ, ppm, TMS): 4.1 (q, COO$\underline{CH_2}$), 3.4 (dd, C$\underline{H_2}$Br), 1.7–2.1 (m, H of cyclopropane), 1.2 (s, CH$_3$ geminals), 1.2 (t, C$\underline{H_3}$—CH$_2$O).

s=singlet, dd=doublet of a doublet, t=triplet, q=quartet, m=multiplet).

EXAMPLE 10 (Method C)

Preparation of (2-carbethoxy-3,3-dimethyl)-cyclopropyl)-methyl-triphenylphosphonium bromide.

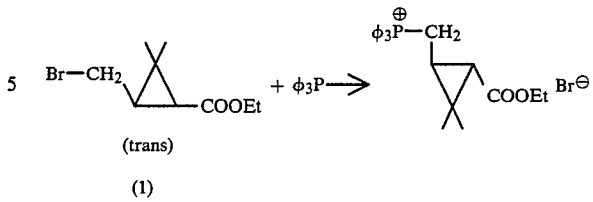

Into a 2 liter autoclave were placed 0.163 mols of 2-bromomethyl-3,3-dimethyl-carbethoxy-cyclopropane-trans (1), 0.18 mols of triphenylphosphine and 500 cc of ethyl ether.

The autoclave was then washed with nitrogen, heated up to about 120° C. (inside pressure about 9.5 atm.) for 50 hours. The mixture was then cooled down and the white solid that was obtained was filtered. There were obtained 0.147 mols corresponding to a yield of 90%. The m.p. was about 182°–184° C.

| Elemental Analysis (percentage): | | | |
|---|---|---|---|
| C, theoretical: | 64.56 | C, found: | 65.20 |
| H, theoretical: | 6.05 | H, found: | 6.08 |
| Br, theoretical: | 16.07 | Br, found: | 16.25 |

EXAMPLE 11 (Method C)

Preparation of 2-bromomethyl-3,3-dimethyl-carbethoxycyclopropane-cis, starting from 6,6-dimethyl-3-oxa-bicyclo(3,1,0)-hexane-(2)-one.

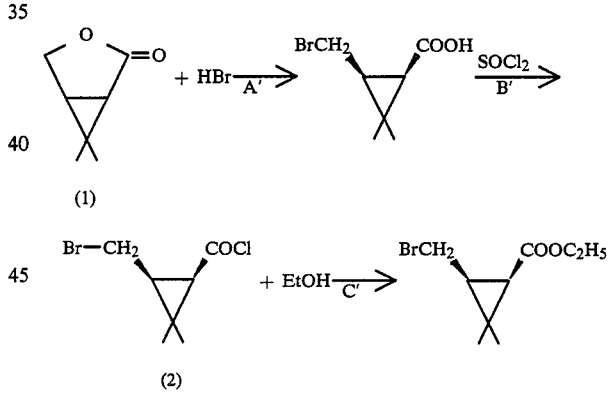

(A') Into a solution of lactone (1) (0.37 mols) and of 60 cc of 99.5% ethanol, were made to bubble through 0.98 mols of gaseous hydrogen bromie. The temperature was rigorously maintained at between 0° and 2° C. (Bubbling time=5 hours). The solution was then kept under stirring at 0° C. for another 19 hours.

Cooling the solution down, there were added 160 cc of water and ice. The resulting white precipitate was filtered. The filtrate was then washed with water until attaining a neutral pH (5 times, each time with 50 cc) and successively was washed with petroleum ether. It was then anhydrified and the petroleum ether was evaporated, thereby obtaining 0.055 mols of 2-bromomethyl-3,3-dimethyl-carbethoxycyclopropane. From the washing waters, by extraction with methylene chloride there were obtained about 3 g of the starting product.

The white solid filtrate which, after drying, weighed 50 g, showed a melting point (m.p.) of 115°–117° C., and proved soluble in 5% bicarbonate.

| The elementary analysis (in percent) was: | |
|---|---|
| theor. C = 40.60; | found C = 40.71 |
| theor. H = 5.35; | found H = 5.37 |
| theor. Br = 38.60; | found Br = 38.54 |

(B') The 2-bromomethyl-3,3-dimethyl-carboxycyclopropane obtained according to point A' (0.18 mols) was dissolved in 180 cc of chloroformium. Thereupon, by dripping, there was added the thionyl chloride (0.36 mols) cooling with water and ice so that the reaction temperature did not exceed 10° C. The reaction mixture was then reflux heated until there is no more development of hydrochloric acid (about 5 hours). It was then evaporated at reduced pressure thereby obtaining a raw oil (yield=about 95%).

The raw product thus obtained partly decomposes by distillation and is then used as such in stage (C). By a distillation test on a reduced quantity, there was obtained an 85% pure product (GLC) with a b.p. (at 0.15 mm Hg)−50°–55° C. IR analysis: 1770 cm$^{-1}$ (C') 0.18 mols—of the raw acyl chloride prepared according to point B', were admixed to 50 cc of anhydrous benzene. While cooling the mixture with water and ice, there were dripped into it 0.36 mols of a 99.9% ethanol.

Once the addition of the ethanol was accomplished, there were dripped in slowly, at about 0° C., 0.18 mols of pyridine. The mixture was then allowed to rest overnight at room temperature and the salt that had formed was filtered. The filtrate, after washing to a neutral pH with water, was anhydrified on sodium sulphate and then evaporated. Thereby were obtained 40 g of oil which was distilled.

B.p. (at 15 mm Hg)=107°–110° C.
IR analysis: 1720 cm$^{-1}$.

EXAMPLE 12

Preparation of β-trifluoromethyl-β-chloro-acrolein.

A mixture of CF$_3$—CCl$_3$ (450 g; 2.4 mols) and n.butylvinyl ether (80 g; 0.8 mols) was irradiated with a mercuryvapor U.V. lamp of the Hanau HP type, model TQ 150, for 1.5 hours at 45° C. The reaction mixture was then distilled in order to remove the unconverted reactants. Thereby was obtained a residue consisting of 1,1,3-trichloro-4,4,4-trifluorobutylbutyl-ether, chromatographically pure (yield=89%).

0.1 mols of this compound were thereupon dripped, at room temperature, into a solution containing 0.1 mols of sodium-carbonate decahydrate in 100 cc of water.

This solution was maintained under stirring for 3 hours. Thereafter the organic phase was separated from the solution and anhydrified and then distilled at atmospheric pressure. The pure product boils at about 70° C. The IR analysis resulted in: 3050, 1685, 1625 cm$^{-1}$.

NMR (CDCl$_3$) (δ, ppm)=6.7 (d,

J=7 Hz), 10.1 (d, CHO, J=7 Hz).
(d=doublet, J=coupling constant).

The preparation was then repeated in the absence of a base, operating in the following way:

50 g (0.174 mols) of 4,4,4-trifluoro-3,3,1-trichlorobutyl-butyl ether were introduced into a 250 ml flask fitted with a stirrer and a reflux condenser. After the addition of 150 ml of water, the content was heated at reflux temperature (temperature of the mixture=about 85° C.) for 1 hour. At this point the flask was connected to a Vigreux column and the content was distilled thereby gathering the fraction that boiled between 71° C. and 75° C.

After anhydrification on Na$_2$SO$_4$ and filtering, there were obtained 15 g of β-trifluoromethyl-β-chloroacrolein.

EXAMPLE 13 (Method C)

This illustrates the preparation of 3-(4',4'-dichlorobutadienyl)-2,2-dimethyl-carbethoxy-cyclopropane (trans).

To a suspension of 0.01 mols of [(2-carbethoxy-3,3-dimethyl)-cyclopropyl]-methyl-triphenylphosphonium bromide in 30 ml of tetrahydrofurane (distilled on lithium-aluminum hydride), at −25° C., by dripping were admixed 0.01 mols of a butyl-lithium solution in hexane (1.5 molar).

The suspension was maintained under stirring for 20 minutes at −20° C. whereafter into it were dripped 0.014 mols of β,β-dichloro-acrolein in 2 ml of tetrahydrofurane. Thus, the temperature was allowed to rise to 0° C.

The mixture was maintained under stirring for 10 minutes and was then cooled down again to −20° C. adding to it 0.01 mols of phosphoric hexamethyltriamide.

The mixture was then maintained under stirring at room temperature 20 minutes. To it was then admixed 10 ml of water and it was then kept under stirring for 2 hours. After this period, the mixture was poured into 50 ml of water, the phases were separated and the organic one was extracted with toluene (2 times, each time with 30 cc of solvent).

The organic phase was thereupon washed with water until attaining a neutral pH. Thereupon it was anhydrified on anhydrous sodium sulphate and evaporated. There were obtained 4.9 g of product (a dark oil) which was then passed through a cylindrical funnel of 5 cm diameter, containing 70 g of alumina. The mixture was then eluted with 100 cc of hexane (1st fraction), then with 200 cc of a mixture hexane-ethyl acetate (9:1) (2nd fraction) and finally with 300 cc of a mixture of hexane-ethyl acetate (7:3) (3rd fraction).

The three fractions were then evaporated separately. The second (about 1.0 g) showed an IR spectrum coherent with the product. According to the GLC there were present two isomers for a total of 50–55% of the fraction.

This product was then bubble distilled (temperature: 120°–140° C.) at a pressure of 1 mm Hg, thereby obtaining the pure product.

IR: 1725, 1625, 1580 cm⁻¹;

| The NMR(δ, ppm, CDCl₃): | |
|---|---|
| 1.10–1.40 | (CH₃) |
| 1.50–1.70 | (m, \–CH–CO) |
| 2.00–2.25 | (m, \–CH–C=C) |
| 4.15 | (q, CH₂O) |
| 5.15–5.85 | (m, C$\underline{H}$=CH—CH=CCl₂) |
| 6.0–6.5 | (m, CH=C$\underline{H}$—CH=CCl₂) |
| 6.6–7 | (m, CH=CCl₂). |

EXAMPLE 14

Preparation of the chloride of 3-(4',4'-dichlorobutadienyl)-2,2-dimethyl-cyclopropanecarboxylic acid (trans), (3):

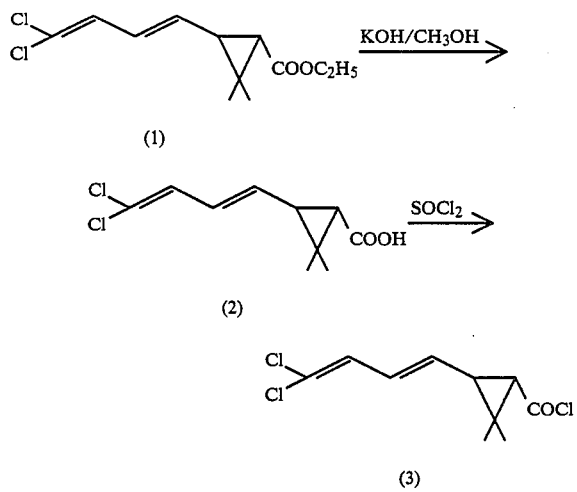

(A) 0.002 mols of the product (1), obtained as described in the preceding Example, were treated with 2.6 ml of a 10% solution of KOH in methanol. It was then reflux heated for 4 hours by a water bath. Thereafter it was cooled down and then poured into 50 cc of water. It was then extracted with toluene (2 times, each time with 20 cc of solvent).

The organic phase was then washed with 20 cc of 10% NaOH. The aqueous phases were then acidified with HCl at 5% concentration, and then extracted with toluene (3 times, each time with 25 cc of solvent). The organic phase was thereupon washed with water until attaining a neutral pH, whereafter it was anhydrified on sodium sulphate and then evaporated, thereby obtaining 0.4 g of an oil consisting of the desired product (2).

IR (cm⁻¹): 3500–2500; 1700–1680; 1430; 1240; 1105; 890; 730; 690.

(B) The raw 3-(4',4'-dichloro-butadienyl)-2,2-dimethylcyclopropanecarboxylic acid (2), obtained by means of the above-described reaction, was dissolved in 3.5 cc of hexane. Then, at 0°–5° C., there were dripped in 3.5 m.mols of thionyl chloride. This mixture was then subjected to reflux and stirring for 4 hours. Thereafter the hexane was decanted from the tars and evaporated at 40° C. under a pressure of 15 mm Hg, thereby obtaining about 0.2 g of chloride of 2,2-dimethyl-3-(4',4'-dichlorobutadienyl)-cyclopropanecarboxylic acid (3).

The IR, γ(C=O): 1765 cm⁻¹, γ(Cl₂C=CH): 1580 cm⁻¹, γ(CH=CH): 1615 cm⁻¹.

EXAMPLE 15

Operating in the same way as that described in Example 14, the following compounds were prepared:

Chloride of 3-(3',4',4'-trichlorobutadienyl)-2,2-dimethylcyclopropanecarboxylic acid (trans) of formula;

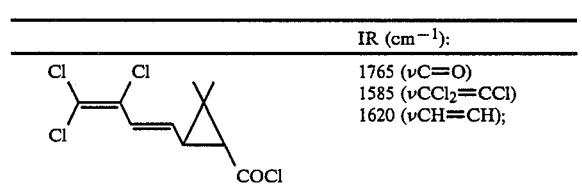

| | IR (cm⁻¹): |
|---|---|
| | 1765 (νC=O) |
| | 1585 (νCCl₂=CCl) |
| | 1620 (νCH=CH); |

Chloride of 3-(5',5',5'-trifluoro-4'-chloro-penta-1',3'-dienyl)-2,2-dimethyl-cyclopropanecarboxylic acid of formula:

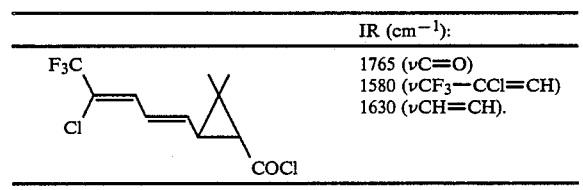

| | IR (cm⁻¹): |
|---|---|
| | 1765 (νC=O) |
| | 1580 (νCF₃—CCl=CH) |
| | 1630 (νCH=CH). |

EXAMPLE 16

Preparation of the α-cyano-3-phenoxybenzyl ester of the (±)-trans-3-(4',4'-dichlorobutadienyl)-2,2-dimethylcyclopropanecarboxylic acid (3) (compound No. 1).

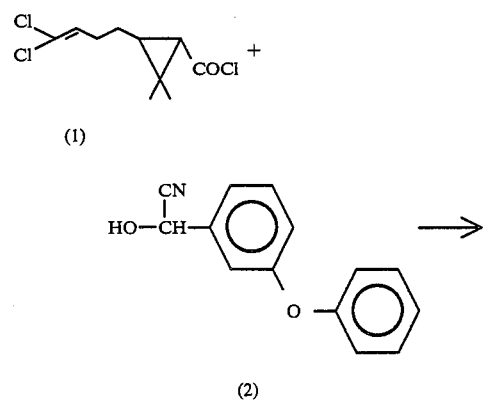

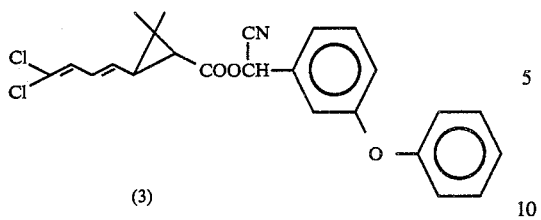

(3)

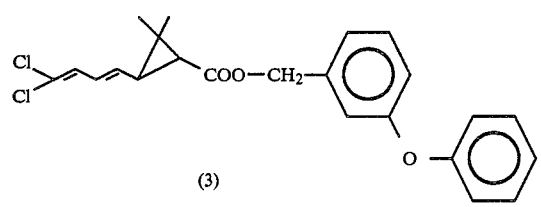

(3)

0.2 g of the acylic chloride (1), prepared as described in Example 15, were diluted with 1 cc of anhydrous ethyl ether. This mixture was cooled down to 0° C. and then there was dripped into it a mixture of the cyanhidrine of phenoxybenzaldehyde (2) (180 mg=about 0.8 m mols) in 0.5 cc of anhydrous ether. This mixture was subjected to stirring at room temperature for 1 hour, after which it was cooled down to 0° C. and into it was dripped a mixture consisting of 0.75 mols of pyridine and 0.5 cc of ether. Thereupon the temperature was allowed to slowly rise. The mixture was then maintained under stirring at room temperature overnight.

The mixture was then diluted with 5 cc of benzene, washed with water up to a neutral pH (2×5 cc), anhydrified, filtered and evaporated whereby there was obtained an oily residue of about 400 mg. Thereupon was rapidly carried out a chromatography with 20 g of silica, eluting with hexane-ethyl acetate (9:1). There were obtained 200 mg of a pure product (3).

GLC titre=90% (glass column, legth=1.2 mt., outside diameter=6 mm, inside diameter=4 mm; packed with Chromosorb W.H.P. 80-100 mesh, covered with silicon oil HCC-W 982; 8% by weight, temperature 280° C., isothermic).

NMR (CDCl₃) δ, ppm (TMS): 1.1–1.4 (CH₃);

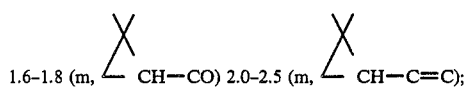

1.6–1.8 (m, CH—CO) 2.0–2.5 (m, CH—C=C);

5.0–5.8 (m, CH=CH—CH=CCl₂); 6.2–6.5 (m, CH—CN and CH=CH—CH=CCl₂); 6.9–7.6 (m, CH=CCl₂ and aromatic protons).

EXAMPLE 17

Preparation of the 3-phenoxy-benzyl ester of (±, trans), 2,2-dimethyl-3-(4′,4′-dichlorobutadienyl)-cyclopropanecarboxylic acid (3) (compound No. 2).

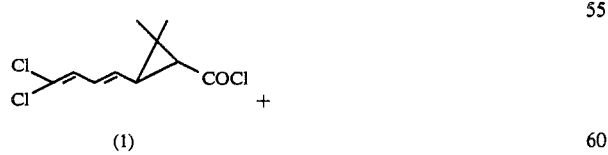

(1)

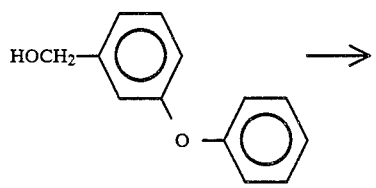

→

0.25 g of compound (1), prepared as described in Example 14, were diluted with 0.5 cc of anhydrous benzene. It was then cooled down to 0° C. and into it there was dripped a mixture consisting of 3-phenoxybenzyl alcohol (2) (0.1 m. mols) and of 0.5 cc of anhydrous benzene. Then, still at 0° C., there was dripped into it a mixture consisting of 0.9 m. mols of pyridine and 0.5 cc of anhydrous benzene. This mixture was then maintained under stirring at room temperature overnight. Thereupon it was washed with water until attaining a neutral pH, anhydrified and finally evaporated, thereby obtaining 300 mg of raw product which was then purified by preparatory chromatography.

GLC: 2 isomers, total 97% (glass column, length 2 meters, outer diameter 6 mm, inner diameter 4 mm; packed with Chromosorb W-HP of 80-100 mesh, covered with 3% b.w. of silicon oil OV-210; isothermic temperature=240° C.).

NMR (CDCl₃) δ, ppm (TMS): 1,1–1,3 (CH₃); 1.5–1.7

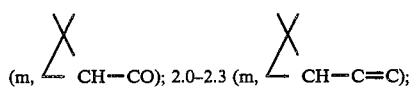

(m, CH—CO); 2.0–2.3 (m, CH—C=C);

5.05 (s, CH₂—O); 5–5.8 (m, CH=CH—CH=CCl₂); 6.2–6.5 (m, CH=CH—CH=CCl₂); 6.8–7.5 (m, CH=CCl₂ and aromatic protons).

EXAMPLE 18

Operating in the same way as that described in Example 17, there was prepared the 3-phenoxyl-benzyl ester of (±) trans-3-(3′,4′,4′-trichlorobutadienyl)-2,2-dimethyl-cyclopropanecarboxylic acid (compound No. 3):

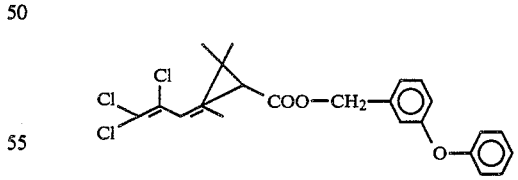

IR (cm⁻¹)=1715, 1620, 1580, 1480, 1250, 1210, 1160, 1110 930, 780 and 690.

| NMR (CDCl₃)δ, ppm (TMS): | |
|---|---|
| 1.2–1.4 | (CH₃), |
| 1.7–1.9 | |

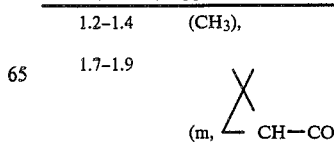

(m, CH—CO

-continued

NMR (CDCl₃)δ, ppm (TMS):

| 2.1-2.4 | 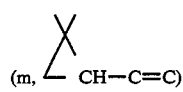 (m, CH—C=C) |
|---|---|
| 5.1 | (s, CH₂O), |
| 5.5-6.2 | (m, CH=CH—CCl=CCl₂) |
| 6.9-7.6 | (m, CH=CH—CCl and aromatic protons) |

EXAMPLE 19

Operating in the same way as described in Example 16, there was prepared α-cyano-3-phenoxy-benzyl ester of the (±)-trans-3-(5',5',5'-trifluoro-4'-chloro-penta-1,3-dienyl)-2,2-dimethyl-cyclopropanecarboxylic acid (compound No. 4) of the formula:

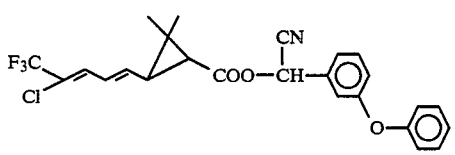

IR (cm⁻¹): 1725 (γC=O); 1630 (γCH=CH).

EXAMPLE 20

Preparation of 3-(E,Z-4',4'-dichloro-2'-bromo-butadienyl)-2,2-dimethyl-carbethoxycyclopropane(-trans):

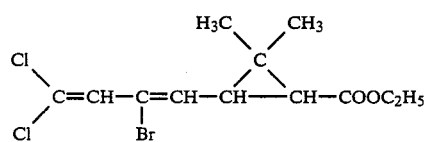

The compound was prepared from the compound of Example 13 [3-(4',4'-dichlorobutadienyl)-2,2-dimethyl-carbethoxycyclopropane] by bromination and dehydrobromination according to conventional methods (Scheme 1c).

IR 1730 cm⁻¹ (γC=O); 1595 cm⁻¹ (γC=C).

EXAMPLE 21

Preparation of the chloride of 3-(E,Z-4',4'-dichloro-2'-bromobutadienyl)-2,2-dimethyl-cyclopropanecarboxylic acid (trans):

$$\underset{Cl}{\overset{Cl}{\diagdown}}C=CH-\underset{Br}{C}=CH-CH\underset{}{\diagup}\overset{H_3C\diagdown \diagup CH_3}{\underset{C}{}}\diagdown CH-COCl$$

The compound has been prepared in an analogous way to that described in Example 14, starting from the corresponding ethyl ester (Example 20).

IR: 1775 cm⁻¹ (γC=O), 1595 cm⁻¹ (γC=C).

EXAMPLE 22

Preparation of 3-phenoxy-benzyl ester of 3-(E,Z-4',4'-dichloro-2'-bromo-butadienyl)-2,2-dimethyl-cyclopropanecarboxylic acid (trans) (compound No. 5):

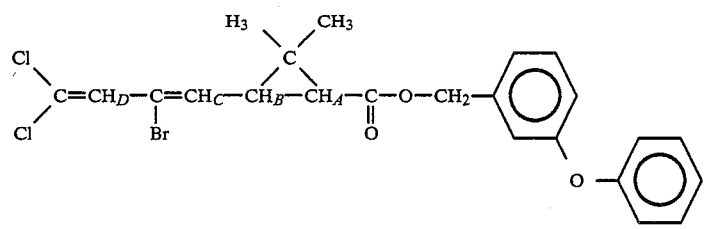

The compound was prepared using the same method as that described in Example 17, starting from the acylchloride of Example 21 and from 3-phenoxy-benzyl alcohol.

IR: 1730 cm⁻¹ (γC=O); 1590 cm⁻¹ (expanded band, γC=C+ aromatics);

| NMR (CDCl₃, TMS): δ (ppm): | 1.17 1.28 | } (6H, geminal methyls) |
|---|---|---|
| | 1.65 | (d, 1H, H$_A$) |
| | 2.02 | (dd, 1H, H$_B$) |
| | 5.10 | (s, 2H, CH₂) |
| | 5.63-6.15 | (d, d, 1H, H$_C$) |
| | 6.40 | (s, 1H, H$_D$) |
| | 6.75-7.55 | (m, 9H, aromatic protons) |
| | $J_{HA-HB} = 6.0$ Hz | |
| | $J_{HB-HD} = 10.0$ Hz | |

(s = singlet, d = doublet, dd = doublet of doublet, m = multiplet, J = coupling constant).

EXAMPLE 23

This illustrates the preparation of the α-cyano-3-phenoxy-benzyl ester of the 3-(4',4'-dichloro-2-bromobutadienyl)-2,2-dimethyl-cyclopropanecarboxylic acid (trans) (compound No. 6).

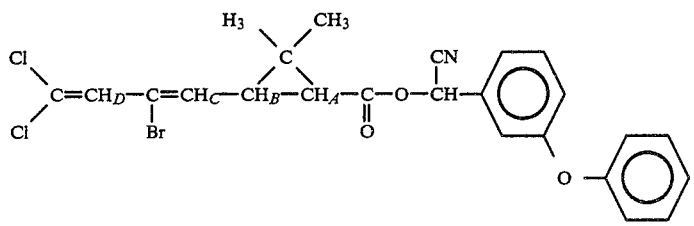

The compound was prepared using the same method as described in Example 16, starting from the acyl-chloride of Example 21 and from α-cyano-3-phenoxy-benzyl alcohol.

IR: 1740 cm$^{-1}$ ($\gamma$C=O), 1590 cm$^{-1}$ (expanded band, $\gamma$C=C+ aromatics);

| NMR: (CDCl$_3$, TMS): | | |
|---|---|---|
| δ (ppm): | 1.0–1.45 | (m, 6H, geminal methyls) |
| | 1.6–2.2 | (m, 1H, H$_A$) |
| | 1.9–2.2 | (m, 1H, H$_B$) |
| | 5.6–6.1 | (d, d, 1H, H$_C$) |
| | 6.3–6.45 | (m, 2H, H$_D$ + CH—CN) |
| | 6.85–7.55 | (m, 9H, aromatic protons) |

(d = doublet; m = multiplet).

EXAMPLE 24

This illustrates the preparation of the α-cyano-3-phenoxy-benzyl ester of the 3-(E,Z-2',4',4'-trichloro-butadienyl)-2,2-dimethyl-cyclopropanecarboxylic acid (trans) (compound No. 7).

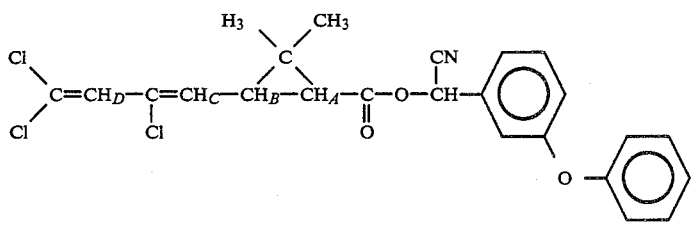

The compound was prepared starting from the ethyl ester of the 3-(E,Z-2',4',4'-trichloro-butadienyl)-2,2-dimethyl-cyclopropanecarboxylic acid (Compound B, Example 7) which was converted to the corresponding acyl chloride, operating in a similar way to that described in Example 14, and then esterified with α-cyano-3-phenoxy-benzyl alcohol operating in a similar way to that described in Example 16.

| NMR (CDCl$_3$, TMS): | | |
|---|---|---|
| δ (ppm): | 1.05–1.45 | (m, 6H, geminal methyls) |
| | 1.57–1.80 | (m, 1H, H$_A$) |
| | 1.80–2.80 | (m, 1H, H$_B$) |
| | 5.59–5.81 | (d, d, H$_D$, E + Z) |
| | 6.35 | (2H, H$_D$ + CH—CN) |
| | 6.87–7.65 | (m, 9H, aromatic protons) |

(d = doublet; m = multiplet).

EXAMPLE 25

This illustrates the preparation of the ethyl ester of 3-(E,Z-4'-chloro-1',3'-pentadienyl)-2,2-dimethyl-cyclopropanecarboxylic acid:

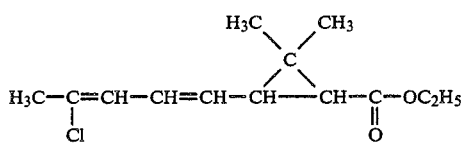

The compound was prepared according to the same procedures that have been described in Example 13, starting from [(2-carboethoxy-3,3-dimethyl)-cyclopropyl]-methyltriphenylphosphorium bromide and from β-methyl-β-chloroacrolein

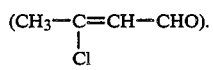

IR: meaningful bands at: 1720, 1620, 1180 and 965 cm$^{-1}$.

EXAMPLE 26

Preparation of the chloride of 3-(E,Z-4'-chloro-1',3'-pentadienyl)-2,2-dimethyl-cyclopropanecarboxylic acid:

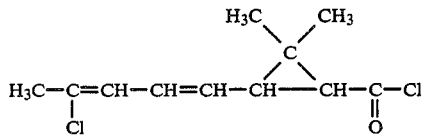

The ethyl ester of Example No. 25 was subjected to an alkaline hydrolysis thereby obtaining the corresponding carboxylic acid [IR 1700 cm$^{-1}$ ($\gamma$C=O)] and this latter compound according to the methods described in Example 14, was treated with thionyl chloride.

IR of acyl-chloride: 1780 cm$^{-1}$ ($\gamma$C=O).

EXAMPLE 27

Preparation of α-cyano-3-phenoxy-benzyl ester of the 3(E,Z-4'-chloro-1',3'-pentadienyl)-2,2-dimethyl-cyclopropanecarboxylic acid (Compound No. 8):

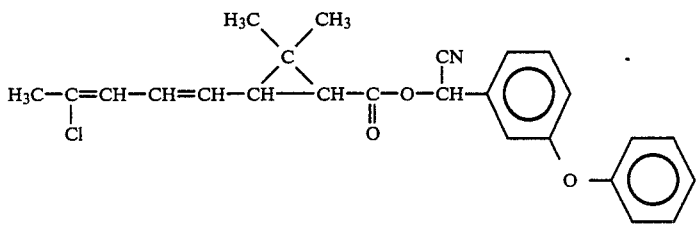

The compound was prepared by operating in an analogous way as that described in Example 16, starting from acyl chloride of Example 26 and from α-cyano-3-phenoxy-benzyl alcohol. The product was obtained in the form of a mixture of cis-trans isomers on the cyclopropane ring, in a ratio of about 1:9.

IR: 1720 cm$^{-1}$ (γC=O).

EXAMPLE 28

Insecticide activity of the compounds of the invention

The compounds of this invention were tested on larvae and adults of the following phytophagouses, according to the following methodologies.

(A) Biological activity on *Macrosiphum euphorbiae* (aphides): Pot-grown potato plants were infested with adult females of aphides and, after a few hours, were besprinkled with a hydroacetonic dispersion of the products under examination.

The mortality percentage was determined 24 hours after treatment (mortality of the aphides on untreated plants was equal to 0).

(B) Biological activity on *Pieris brassicae* (Lepidoptera): Cut cauliflower leaves were submitted to besprinkling with a hydroacetonic dispersion of the products under examination.

After drying, the leaves were infested with 5-days old larvae. The mortality percentage of said larvae (mortality on untreated leaves=0) was determined 48 hours after treatment.

(C) Biological activity on *Leptinotarsa decemlineata* (Coleoptera): Small pot-grown potato plants were infested with 4-day old larvae and subsequently subjected to besprinkling with a hydroacetonic dispersion of the products under examination. The mortality percentage (untreated plants, mortality=0) was determined 48 hours after the treatment.

(D) Biological activity on *Musca domestica* (Diptera): 4-day old adults were treated, by topical application with a microsyringe, with an acetonic solution of the products under examination.

The mortality percentage (mortality of the insects treated only with acetone=0) was determined 24 hours after treatment.

(E) Biological activity on *Blatta orientalis* (Orthoptera): The bottom and walls of crystallizers of glass were uniformly treated with an acetonic solution of the products under examination.

After evaporation of the solvent in each crystallizer there were introduced 80–100 days old neanides, thereupon closing the crystallizers with a metal net cover. Twenty-four hours after treatment the insects were transferred in similar, untreated crystallizers and suitably fed.

The mortality percentage (mortality of untreated insects=0) was determined 48 hours after the start of the treatment.

(F) Biological activity on *Tetranychus urticae* adults (Acari): Bean leaf discs were infested with adult acari and successively besprinkled with a hydroacetonic dispersion of the products under examination.

The mortality percentage was determined 24 hours after treatment (mortality of the acari on untreated foliar disc=0).

(G) Biological activity on *Spodoptera littoralis*: Cut tobacco leaves were besprinkled with a hydroacetonic dispersion of the products under examination. After drying, the leaves were infested with 5-day old larvae. The percentage of mortality of the larvae was determined 48 hours after treatment. (The mortality of the larvae on untreated leaves=0).

(H) Biological activity on *Tetranychus urticae* eggs (Acari): Bean leaf discs, previously infested with acari eggs, were treated by besprinkling with a hydroacetonic dispersion of the products under examination. The percentage of unhatched eggs (equivalent to the mortality percentage) was evaluated, 6 days after treatment, in comparison with the percentage of unhatched eggs on the untreated foliar discs.

The biological activity data of some representative compounds have been recorded on the following Table 1 and are expressed as a mortality percentage at the indicated dose.

TABLE 1

Biological activity of compounds of the invention expressed as percentage of mortality of the pests at the indicated doses.

| Compound No. (example No.) | Macrosiphum. e. (0.1°/$_{oo}$) | Pieris b. (0.1°/$_{oo}$) | Leptinotarsa d. (0.1°/$_{oo}$) | Spodoptera l. (0.1°/$_{oo}$) | Musca d. (0.1γ/ins.) | Tetranichus u. (adults) (0.1°/$_{oo}$) | Blatta o. (0.1°/$_{oo}$) |
|---|---|---|---|---|---|---|---|
| 1 (16) | 100 | 100 | 100 | 100 | 100 | 100 | 100 |
| 2 (17) | 80 |  | 62 | 100 | 100 |  |  |
| 3 (18) |  |  | 90 | 100 |  |  |  |
| 4 (19) | 100 | 100 | 100 | 100 | 100 | 70 | 100 |
| 6 (23) | 100 | 100 | 100 | 100 | 100 |  | 100 |
| 7 (24) | 100 | 100 | 100 | 86 | 100 | 53 |  |

TABLE 1-continued

| Biological activity of compounds of the invention expressed as percentage of mortality of the pests at the indicated doses. | | | | | | | |
|---|---|---|---|---|---|---|---|
| Compound No. (example No.) | Macrosiphum. e. (0.1°/oo) | Pieris b. (0.1°/oo) | Leptinotarsa d. (0.1°/oo) | Spodoptera l. (0.1°/oo) | Musca d. (0.1γ/ins.) | Tetranichus u. (adults) (0.1°/oo) | Blatta o. (0.1°/oo) |
| 8 (27) | 100 | 100 | 100 | 100 | | 40 | 100 |

In the following Table 2 are reported the biological activity data against acari eggs (*Tetranichus urticae*) of Compound No. 4 (Example 19), in comparison with that of known pyrethroids.

TABLE 2

| Compound | Dose (%) 0.1 | 0.05 |
|---|---|---|
| 4 | 100 | 100 |
| Permethrin[a] | 18 | 0 |
| Cipermethrin[b] | 11 | 0 |
| Decamethrin[c] | 0 | 0 |
| Phenvalerate[d] | 18 | 0 |

[a]Permethrin: 3-phenoxy-benzyl ester of 2,2-dimethyl-3-(β,β-dichlorovinyl)-cyclopropanecarboxylic acid;
[b]Cipermethrin: α-cyano-3-phenoxy-benzyl ester of 2,2-dimethyl-3-(β,β-dichlorovinyl)-cyclopropane-carboxylic acid;
[c]Decamethrin: α-cyano-3-phenoxy-benzyl ester of 2,2-dimethyl-3-(β,β-dibromovinyl)-cyclopropane-carboxylic acid;
[d]Phenvalerate: α-cyano-3-phenoxy-benzyl ester of 1-(4'-chlorophenyl)-2-methyl-butyric acid.

We claim:

1. A compound having the formula:

$$R^1\phantom{xx}R^4\phantom{xxxxx}H_3C\phantom{x}CH_3$$
$$\phantom{xxx}\diagdown\phantom{x}|\phantom{xxxxxxx}\diagdown\diagup$$
$$\phantom{xxxxx}C=C-C=CH-CH\phantom{xx}C\phantom{xx}CH-C-R$$
$$\phantom{xxx}\diagup\phantom{x}|\phantom{xxxxxxxxxxxxxxxxxxxxxx}\|$$
$$R^2\phantom{xx}R^3\phantom{xxxxxxxxxxxxxxxxxxxxxxxxx}O$$

wherein:

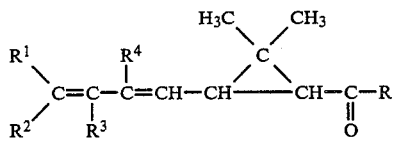

($R^5$=H, CN, —C≡CH)
$R^1$=F, Cl, Br, $CH_3$, $CF_3$
$R^2$=F, Cl, Br, $CF_3$
$R^3$=H, F, Cl, Br, $CF_3$
$R^4$=H, F, Cl, Br, $CF_3$ or $R^2$ and $R^3$ together form a third bond between the carbon atoms to which they are bonded.

2. A compound according to claim 1, wherein:

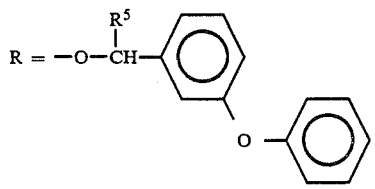

and $R^5$=H, CN.

3. A compound according to claim 2 which is the α-cyano-3-phenoxy-benzyl ester of 3-(4',4'-dichlorobutadienyl)-2,2-dimethylcyclopropanecarboxylic acid.

4. A compound according to claim 2 which is the 3-phenoxy-benzyl ester of 3-(4',4'-dichlorobutadienyl)-2,2-dimethylcyclopropanecarboxylic acid.

5. A compound according to claim 2 which is the 3-phenoxy-benzyl ester of 3-(3',4',4'-trichlorobutadienyl)-2,2-dimethyl-cyclopropanecarboxylic acid.

6. A compound according to claim 2 which is the α-cyano-3-phenoxy-benzyl ester of 3-(5',5',5'-trifluoro-4'-chloro-penta-1',3'-dienyl)-2,2-dimethylcyclopropanecarboxylic acid.

7. A compound according to claim 2 which is the 3-phenoxy-benzyl ester of 3-(4',4'-dichloro-2'-bromobutadienyl)-2,2-dimethylcyclopropanecarboxylic acid.

8. A compound according to claim 2 which is the α-cyano-3-phenoxy-benzyl ester of 3-(4',4'-dichloro-2'-bromo-butadienyl)-2,2-dimethylcyclopropanecarboxylic acid.

9. A compound according to claim 2 which is the α-cyano-3-phenoxy-benzyl ester of 3-(2',4',4'-trichlorobutadienyl)-2,2-dimethyl-cyclopropanecarboxylic acid.

10. A compound according to claim 2 which is the α-cyano-3-phenoxy-benzyl ester of 3-(4''chloro-1',3'-pentadienyl)-2,2-dimethylcyclopropane carboxylic acid.

11. A method for fighting infestations by insects or acari, characterized in that an effective amount of one or more of the compounds of claim 1, having the specified formula wherein:

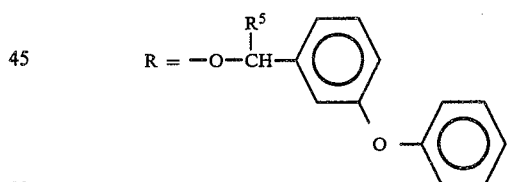

are distributed as such or in the form of suitable composition in the habitat of the insects or acari.

12. Insecticide and/or acaricide compositions having as an active principle one or more compounds according to claim 1 wherein

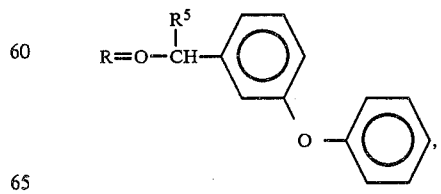

13. A compound selected from the group consisting of 3-(buta-1',3'-dienyl)-cyclopropane-1-carboxylic acid compounds of all of the possible stereoisomers or mixtures of stereoisomers of compounds of the formula:

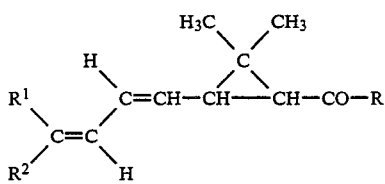

wherein $R^1$ and $R^2$ are individually a halogen and R is selected from the group consisting of:

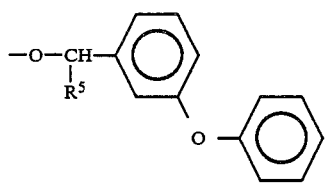

wherein $R^5$ is selected from the group consisting of hydrogen, —CN and —C≡CH.

14. A compound of claim 13 where $R^1$ and $R^2$ are the same and are selected from the group consisting of bromine and chlorine.

15. A compound of claim 13 wherein R is α-cyano-3-phenoxy-benzoxy.

16. A composition for combating pests of vegetables and warm-blooded animals comprising a pesticidally effective amount of at least one compound of claim 13 and an inert carrier.

17. An insecticidal composition comprising an insecticidal effective amount of at least one compound of claim 13 and an inert carrier.

18. A composition of claim 17 wherein $R^1$ and $R^2$ are the same and are selected from the group consisting of bromine and chlorine.

19. A composition of claim 17 wherein R is α-cyano-3-phenoxy-benoxy.

20. A method of combating insects comprising contacting insects with an insecticidally effective amount of at least one compound of claim 13.

21. A method of claim 20 wherein $R^1$ and $R^2$ are the same and are selected from the group consisting of bromine and chlorine.

22. A method of claim 21 wherein R is α-cyano-3-phenoxy-benoxy.

* * * * *